(12) United States Patent
Sasao et al.

(10) Patent No.: US 11,639,402 B2
(45) Date of Patent: May 2, 2023

(54) POLYMER FOR PATTERN FORMING MATERIAL

(71) Applicant: Kioxia Corporation, Tokyo (JP)

(72) Inventors: Norikatsu Sasao, Kawasaki Kanagawa (JP); Koji Asakawa, Kawasaki Kanagawa (JP); Shinobu Sugimura, Yokohama Kanagawa (JP)

(73) Assignee: Kioxia Corporation, Tokyo (JP)

( * ) Notice: Subject to any disclaimer, the term of this patent is extended or adjusted under 35 U.S.C. 154(b) by 362 days.

(21) Appl. No.: 16/814,030

(22) Filed: Mar. 10, 2020

(65) Prior Publication Data

US 2021/0070898 A1    Mar. 11, 2021

(30) Foreign Application Priority Data

Sep. 11, 2019   (JP) .............................. JP2019-165444

(51) Int. Cl.
*C08F 20/30* (2006.01)
*C07C 69/56* (2006.01)
(Continued)

(52) U.S. Cl.
CPC .............. *C08F 20/30* (2013.01); *C07C 69/76* (2013.01); *C08F 12/22* (2013.01); *C09D 125/18* (2013.01);
(Continued)

(58) Field of Classification Search
CPC .......... C08F 20/30; C08F 12/22; C07C 69/76; C09D 1125/18; C09D 133/14; H01L 21/0271
(Continued)

(56) References Cited

U.S. PATENT DOCUMENTS 5,079,600 A   1/1992  Schnur et al.
7,122,293 B2 * 10/2006 Sugasaki ............... B41C 1/1008
                                                          430/287.1
(Continued)

FOREIGN PATENT DOCUMENTS

CN   101673053 A   3/2010
CN   109265584 A   1/2019
(Continued)

OTHER PUBLICATIONS

Biswas et al., "New Insight into the Mechanism of Sequential Infiltration Synthesis from Infrared Spectroscopy," Chem. Mater., 26:6135-41 (2014).

(Continued)

*Primary Examiner* — Michael M. Bernshteyn
(74) *Attorney, Agent, or Firm* — Finnegan, Henderson, Farabow, Garrett & Dunner, LLP

(57) ABSTRACT

A pattern forming material is configured to use for forming an organic film on a film to be processed, patterning the organic film, and then forming a composite film by infiltrating a metallic compound into the patterned organic film. The pattern forming material contains a polymer including a monomer unit represented by a general formula (1) described below,

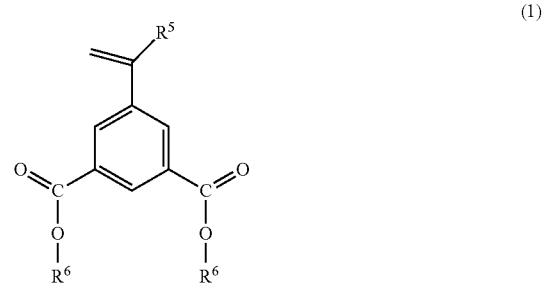

(1)

wherein, $R^5$ is a hydrogen atom or a methyl group, each $R^6$ independently is an ethyl group, an n-propyl group, an isopropyl group, an n-butyl group, an isobutyl group, or an s-butyl group, and a monomer unit derived from a compound represented by a general formula (2) described below, (Continued)

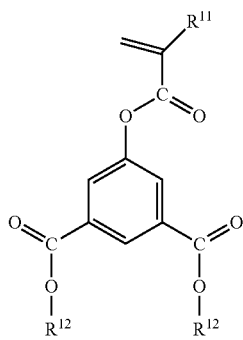

wherein, $R^{11}$ is a hydrogen atom or a methyl group, each $R^{12}$ independently is a methyl group, an ethyl group, an n-propyl group, an isopropyl group, an n-butyl group, an isobutyl group, an s-butyl group, or a t-butyl group.

1 Claim, 2 Drawing Sheets

(51) Int. Cl.
| | | |
|---|---|---|
| *H01L 21/02* | (2006.01) | |
| *C09D 125/18* | (2006.01) | |
| *C09D 133/14* | (2006.01) | |
| *C08F 12/22* | (2006.01) | |
| *C07C 69/76* | (2006.01) | |
| *H01L 21/027* | (2006.01) | |

(52) U.S. Cl.
CPC ........ *C09D 133/14* (2013.01); *H01L 21/0271* (2013.01)

(58) Field of Classification Search
USPC ........................................................ 438/780
See application file for complete search history.

(56) References Cited

U.S. PATENT DOCUMENTS

| | | |
|---|---|---|
| 7,425,399 B2 | 9/2008 | Kishioka et al. |
| 9,487,600 B2 | 11/2016 | Darling et al. |
| 2005/0095529 A1* | 5/2005 | Sugasaki ............... C08F 220/40 430/270.1 |
| 2008/0197322 A1* | 8/2008 | Shipway ............... G03C 1/733 252/301.35 |
| 2013/0288180 A1 | 10/2013 | Hatakeyama et al. |
| 2018/0374695 A1 | 12/2018 | Yamada et al. |
| 2020/0006076 A1 | 1/2020 | Sasao et al. |
| 2020/0291155 A1 | 9/2020 | Sasao et al. |

FOREIGN PATENT DOCUMENTS

| | | | |
|---|---|---|---|
| JP | 2001-310331 A | 11/2001 | |
| JP | 4171920 B2 | 10/2008 | |
| JP | 5333737 B2 | 11/2013 | |
| JP | 2015-38534 A | 2/2015 | |
| JP | 2015038534 A * | 2/2015 | ................ G03F 7/11 |

OTHER PUBLICATIONS

Jun-Feng Zheng et al., "Side-Chain Jacketed Liquid Crystalline Polymer Forming Double-Chain Supramolecular Column and Hexagonal Superlattice", Macromolecules, vol. 51, No. 17, pp. 6949-6957 and Table 1 (2018).

\* cited by examiner

POLYMER FOR PATTERN FORMING MATERIAL

CROSS REFERENCE TO RELATED APPLICATION

This application is based upon and claims the benefit of priority from Japanese Patent Application No. 2019-165444, filed on Sep. 11, 2019; the entire contents of which are incorporated herein by reference.

FIELD

Embodiments described herein relate generally to a compound, a polymer, a pattern forming material, and a manufacturing method of a semiconductor device.

BACKGROUND

In a manufacturing process of a semiconductor device, a demand for a technique of forming a pattern having a high aspect ratio is increasing. High etch resistance is demanded for a mask pattern used for such a process because the mask pattern is exposed to etching gas for a long time.

SUMMARY

The embodiment provides a compound represented by a general formula (1) described below (hereinafter, a compound (1)), a compound represented by a general formula (2) described below (hereinafter, a compound (2)), and a polymer containing at least one of monomer unit selected from a monomer unit derived from the compound (1) and a monomer unit derived from the compound (2).

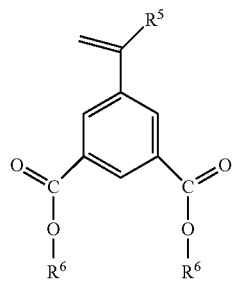

(1)

wherein, $R^5$ is a hydrogen atom or a methyl group, each $R^6$ independently is an ethyl group, an n-propyl group, an isopropyl group, an n-butyl group, an isobutyl group, or an s-butyl group.

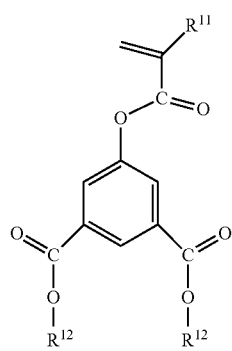

(2)

wherein, $R^{11}$ is a hydrogen atom or a methyl group, each $R^{12}$ independently is a methyl group, an ethyl group, an n-propyl group, an isopropyl group, an n-butyl group, an isobutyl group, an s-butyl group, or a t-butyl group.

DETAILED DESCRIPTION

Figure 1A:
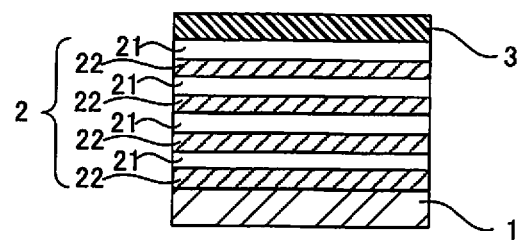
FIG. 1A to FIG. 1E illustrate processes of a manufacturing method of a semiconductor device according to an embodiment.

Hereinafter, embodiments of the present invention will be explained in detail with reference to the drawings. Note that the present invention is not limited by the following embodiments. Further, components in the following embodiments include the one easily assumed by those skilled in the art or substantially the same one.

A polymer is formed by polymerization of monomers and is constituted by repeating units derived from a monomer. In this specification, the repeating unit constituting the polymer is referred to as a monomer unit. The monomer unit is a unit derived from a monomer, and a constituent monomer of the monomer unit means a monomer forming the monomer unit by the polymerization.

In this specification, a compound represented by a general formula (1) is also mentioned as a compound (1). A monomer unit represented by a general formula (3) is also mentioned as a monomer unit (3). Furthermore, a monomer unit derived from the compound (1) is also denoted as a monomer unit (1). Similarly, a constituent monomer of the monomer unit (3) is denoted as a monomer (3). Also in a case of a compound and a monomer unit represented by another general formula or chemical structural formula, the compound and the monomer unit are similarly represented by marks of the general formula or the chemical structural formula.

In consideration of the above-described demand, the present inventors have found a new polymerizable compound capable of producing a polymer which is useful for a pattern forming material. Furthermore, the present inventors have found that a mask pattern with high etch resistance can be obtained by forming an organic film from the pattern forming material containing the polymer of the polymerizable compound containing the compound having a specific substructure, patterning the organic film, and then using a composite film obtained by infiltrating a metallic compound into the organic film as the mask pattern. Infiltrating a metallic compound into an organic film is hereinafter referred as "metallization". Concretely, the metallization can be performed by binding a metallic compound to the organic film having the moiety to which the metallic compound can be bonded. After bonding, the metallic compound may be subjected to post-treatment such as oxidation, for example. Hereinafter, a pattern forming material containing a specific polymer according to the embodiment will be explained.

A compound (1) of the embodiment is represented by a general formula (1) described below.

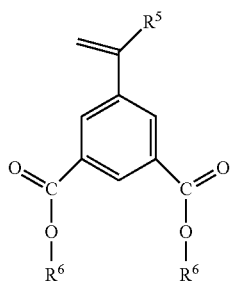

In the general formula (1), $R^5$ is a hydrogen atom or a methyl group, each $R^6$ independently is an ethyl group, an n-propyl group, an isopropyl group, an n-butyl group, an isobutyl group, or an s-butyl group.

In the compound (1), $R^5$ is preferably a hydrogen atom in terms of manufacturability. In the compound (1), two of $R^6$ may be the same or different, but these are preferably the same in terms of manufacturability.

A method producing the compound (1) is not particularly limited. Concretely, the compound (1) can be synthesized from a precursor of the compound (1) where $R^6$ in the general formula (1) is a hydrogen atom by a generally known method and substituting the hydrogen atom with an ethyl group, an n-propyl group, an isopropyl group, an n-butyl group, an isobutyl group, or an s-butyl group.

For example, when $R^5$ in the compound (1) is a hydrogen atom, the precursor can be synthesized according to a report from Yiding Xu and others (Macromolecules 2009, 42(7), 2542-2550). A process to obtain the compound (1) (where $R^5$ is the hydrogen atom) from the precursor according to the report is illustrated in a reaction path (1) described below. In the reaction path (1), the precursor is represented by a chemical structural formula F. In the reaction path (1), $R^6$ refers the same as $R^6$ in the general formula (1).

Reaction path (1)

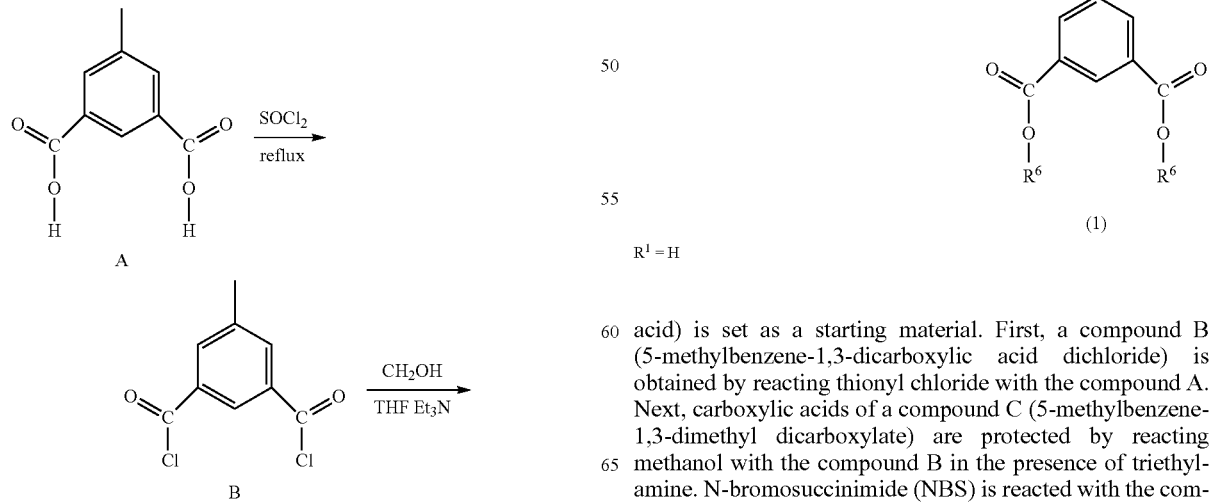

acid) is set as a starting material. First, a compound B (5-methylbenzene-1,3-dicarboxylic acid dichloride) is obtained by reacting thionyl chloride with the compound A. Next, carboxylic acids of a compound C (5-methylbenzene-1,3-dimethyl dicarboxylate) are protected by reacting methanol with the compound B in the presence of triethylamine. N-bromosuccinimide (NBS) is reacted with the compound C in a carbon tetrachloride solvent to brominate a methyl group at the 5 position to obtain a benzylbromo derivative (a compound D), followed by a reaction with triphenylphosphine (PPh3) to obtain a compound E (a benzyltriphenylphosphonium bromide derivative).

A compound F (5-vinylbenzene-1,3-dicarboxylic acid) is obtained as a precursor of the compound (1) (where $R^1$ is a hydrogen atom) by forming a vinyl group in compound E by applying formaldehyde in the presence of sodium hydroxide which simultaneously deprotects the protected dicarboxylic acid by the methyl group.

The obtained 5-vinylbenzene-1,3-dicarboxylic acid was dissolved in DMF (N,N-dimethyl formaldehyde) together with N, N'-carbonyldiimidazole in a small excess. Alcohol, represented in $R^6$OH is reacted at the room temperature in DMF in the presence of 1.8-diazabicyclo[5.4.0]-7-undecene (DBU) to obtain 5-vinyl-1,3-bisalkyl isophthalate (the alkyl group is $R^6$).

$R^6$ is an ethyl group, an n-propyl group, an isopropyl group, a n-butyl group, an isobutyl group, or an s-butyl group. In the compound (1) (where $R^1$ is the hydrogen atom), when $R^6$ is an ethyl group, 5-vinyl-1,3-bis(ethyl) isophthalate is obtained by using ethyl alcohol as the alcohol. In the compound (1) (where $R^5$ is a hydrogen atom), when $R^6$ is an n-propyl group, 5-vinyl-1,3-bis(n-propyl) isophthalate is obtained by using n-propyl alcohol as the alcohol.

In the compound (1) (where $R^5$ is a hydrogen atom), when $R^6$ is an isopropyl group, 5-vinyl-1,3-bis(isopropyl)isophthalate is obtained by using isopropyl alcohol as the alcohol. In the compound (1) (where $R^5$ is a hydrogen atom), when $R^6$ is a n-butyl group, 5-vinyl-1,3-bis(n-butyl)isophthalate is obtained by using n-butyl alcohol as the alcohol. In the compound (1) (where $R^5$ is a hydrogen atom), when $R^6$ is an isobutyl group, 5-vinyl-1,3-bis(isobutyl)isophthalate is obtained by using isobutyl alcohol as the alcohol. In the compound (1) (where $R^5$ is a hydrogen atom), when $R^6$ is a s-butyl group, 5-vinyl-1,3-bis(s-butyl)isophthalate is obtained by using s-butyl alcohol as the alcohol.

The compound (2) of the embodiment is represented by a general formula (2) described below.

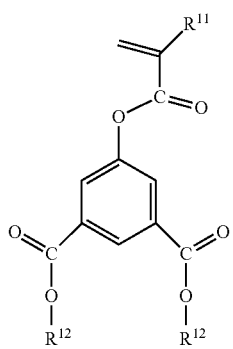

(2)

In the general formula (2), $R^{11}$ is a hydrogen atom or a methyl group, each $R^{12}$ independently is a methyl group, an ethyl group, an n-propyl group, an isopropyl group, an n-butyl group, an isobutyl group, an s-butyl group, or a t-butyl group.

In the compound (2), two of $R^{12}$ may be the same or different, but these are preferably the same in terms of manufacturability.

A method producing the compound (2) is not particularly limited. Concretely, the compound (2) can be synthesized by reacting a compound 1 ((meth)acrylic acid chloride) with a compound G (5-hydroxy-1,3-dicarboxylic acid dialkyl ester (an alkyl group is $R^2$)) in the presence of triethylamine by a generally known method according to a reaction formula (2) described below.

In the reaction formula (2), $R^{11}$ and $R^{12}$ refer the same as $R^{11}$ and $R^{12}$ in the general formula (2). Note that (meth) acrylic acid in this specification is a generic name of acrylic acid and methacrylic acid. Likewise, (meth)acrylate is a generic name of acrylate and methacrylate.

Reaction formula (2)

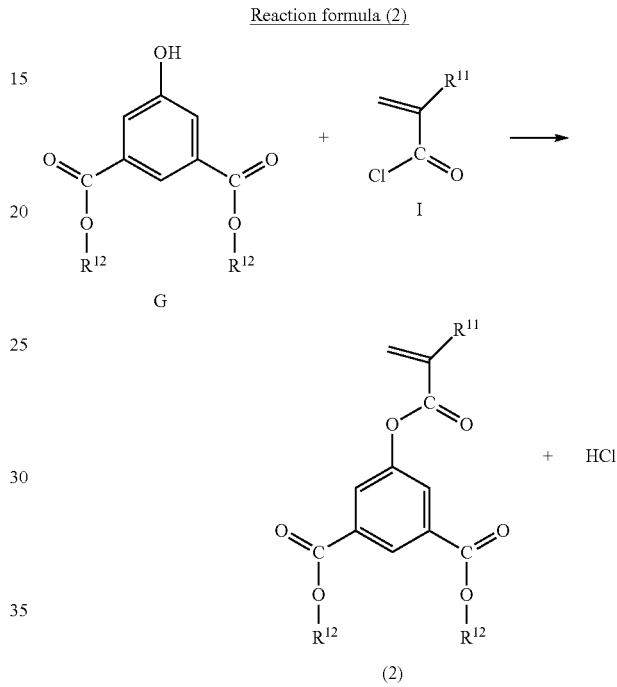

[Polymer]

A polymer of the embodiment is a polymer (hereinafter, it is also mentioned as a polymer Z) containing at least one of monomer unit selected from a monomer unit derived from the compound (1) and a monomer unit derived from the compound (2).

The polymer Z may contain at least one selected from the monomer unit (1) and the monomer unit (2) among all monomer units constituting the polymer Z. The polymer Z may be a polymer (hereinafter, called a polymer Z1) which contains the monomer unit (1) and does not contain the monomer unit (2), a polymer (hereinafter, called a polymer Z2) which contains the monomer unit (2) and does not contain the monomer unit (1), or a polymer (hereinafter, called a polymer Z12) which contains both the monomer unit (1) and the monomer unit (2).

The polymer Z1 may contain only one kind of monomer unit (1) or two or more kinds of monomer units (1). A content ratio of the monomer unit (1) in the polymer Z1 is preferably 50 to 100 mol %, and more preferably 90 to 100 mol % with respect to all the monomer units constituting the polymer Z1.

Similarly, the polymer Z2 may contain only one kind of monomer unit (2) or may contain two or more kinds. A content ratio of the monomer unit (2) in the polymer Z2 is preferably 50 to 100 mol %, and more preferably 90 to 100 mot % with respect to all monomer units constituting the polymer Z2.

Each of the monomer unit (1) and the monomer unit (2) contained in the polymer Z12 may be only one kind or may be two or more kinds. A total content ratio of the monomer unit (1) and the monomer unit (2) in the polymer Z12 is preferably 50 to 100 mol %, and more preferably 90 to 100 mol % with respect to all monomer units constituting the polymer Z12.

When the polymer Z contains other monomer unit than the monomer unit (1) and the monomer unit (2), the other monomer unit is not particularly limited. Examples of the other monomer unit include, for example, styrene, methyl methacrylate, glycidyl methacrylate, methacrylic acid, acrylic acid, and so on.

The polymer can be synthesized from the constituent monomers of the monomer unit by a generally known method such as, for example, bulk polymerization, solution polymerization, emulsion polymerization, suspension polymerization. The solution polymerization is preferred in terms of redissolution to a solvent after polymerization as well as eliminating any possible impurities such as an emulsifier and water. When the polymer Z is synthesized by solution polymerization, normally, monomers are dissolved in a polymerization solvent and polymerized in the presence of an initiator. Polymerization conditions such as an amount of the polymerization solvent, polymerization temperature, and polymerization time are appropriately selected according to the monomer, a molecular weight of the polymer Z to be synthesized, and the like.

[Pattern Forming Material]

A pattern forming material of the embodiment (hereinafter, mentioned as "this pattern forming material".) contains a polymer (hereinafter, also mentioned as a polymer X.) including a monomer unit represented by a general formula (3) described below.

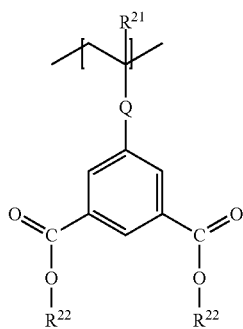

(3)

In the general formula (3), $R^{21}$ is a hydrogen atom or a methyl group, each $R^{22}$ independently is a hydrocarbon group having 2 to 14 carbon atoms where a carbon is primary carbon, secondary carbon or tertiary carbon, Q is a single bond or a hydrocarbon group having 1 to 20 carbon atoms which may include an oxygen atom, a nitrogen atom, or a sulfur atom between carbon-carbon atoms or at a bond terminal, and a halogen atom may be substituted for the hydrogen atom.

In the monomer unit (3), two of $R^{22}$ may be the same or different, but these are preferably the same in terms of manufacturability of the monomer (3).

The monomer unit (3) has a structure having a benzene ring at a terminal of a side chain, and an ester of a carboxyl group at each of the two position and the five position of the benzene ring. In the ester, $R^{22}$ being a group bonding to the oxygen atom next to the carbonyl group is the hydrocarbon group having 2 to 14 carbon atoms. Further, in $R^{22}$, the α carbon, that is, the carbon atom which bonds to the oxygen atom next to the carbonyl group is a primary carbon, a secondary carbon or a tertiary carbon.

The side chain as stated above in the monomer unit (3) enables to obtain a composite film where a metallic compound is firmly bonded to an organic film that is obtained from this pattern forming material as described below.

This pattern forming material is used to form an organic film on a film that is to be processed which is provided with a substrate (the substrate having the film to be processed). This pattern forming material is contained in a later-described composition for pattern formation of the embodiment together with, for example, an organic solvent, and coated on the film that is to be processed by using the composition to form the organic film.

The organic film may be formed of this pattern forming material itself or may be formed by the reaction of components contained by this pattern forming material. After the organic film is patterned, a composite film is formed by binding a metallic compound to the monomer unit (3) in the organic film. Then, the composite film is used as a mask pattern, and the above-described film that is to be processed is processed.

In the polymer X, a reaction where the metallic compound is bonded to the monomer unit (3) is, for example, a reaction represented by a reaction formula (F) or a reaction formula (G) described below. In each of these reaction formulas, $R^{21}$ and Q refer the same as $R^2$ and $R^3$ in the general formula (3), and n represents the number of repetitions of the monomer unit (3) in the polymer X.

The reaction represented by each of the reaction formula (F) and the reaction formula (G) is a reaction example of using trimethylaluminum (TMA) as the metallic compound. $R^{22}$ in the monomer unit (3) is represented by $-CR^1R^2R^3$ (where $R^1$, $R^2$, and $R^3$ each independently represent a hydrogen atom or a hydrocarbon group, wherein at least one of these is a hydrocarbon group, and the total number of carbons is 1 to 13.). In each of the reaction formula (F) and the reaction formula (G), $R^1$ of the monomer unit (3) is a hydrocarbon group, $R^2$ and $R^3$ are hydrogen atoms or hydrocarbon groups, and the bonding of TMA to the monomer unit (3) is explained.

As represented by the reaction formula (F), when TMA is set to react with the monomer unit (3) in the polymer X, Al of TMA is coordinated to an unshared electron pair of =O of two carbonyl groups held by the monomer unit (3). As TMA is coordinated to the unshared electron pair, bond to a primary, secondary or tertiary hydrocarbon group ($-CR^1R^2R^3$) ester-bonded to a side-chain terminal of the monomer unit (3) is presumably weakened. The result shows that $-CR^1R^2R^3$ is cleaved from the monomer unit (3), and a monomer unit represented by a general formula (3') where Al of TMA is bonded to each of two oxygen atoms derived from ester is formed.

The cleaved hydrocarbon group is described as $R^{1'}=CR^2R^3$ in the reaction formula (F). Here, $R^{1'}$ is a group where one hydrogen atom has fallen off from $R^1$. Though a leaving group is described as $R^{1'}=CR^2R^3$ in the reaction formula (F) for convenience, there can also be cases of $R^1C=R^{2'}R^3$ ($R^{2'}$ is a group where one hydrogen atom has fallen off from $R^2$) and $R^1C=R^{3'}R^2$ ($R^{3'}$ is a group where one hydrogen atom has fallen off from $R^3$). Thus, a hydrogen atom comes off from the leaving group to become alkene, which is cleaved off. It is assumed that hydrogen which has come off from the leaving group is substituted to a methyl group of TMA.

When the metallic compound is bonded to the monomer unit (3) in the polymer X, the leaving hydrocarbon group can also be considered as the reaction represented by the following reaction formula (G) aside from a process of the reaction formula (F). That is, as represented by the reaction formula (G), it can be thought that the hydrocarbon group is cleaved off from the monomer unit (3) as $R^1C^1R^2R^3$ for convenience, and is bonded to $(CH_3)^-$ which is cleaved off from TMA which forms $R^1C(CH_3)R^2R^3$, and cleaved off from the main chain Reaction formula (F)

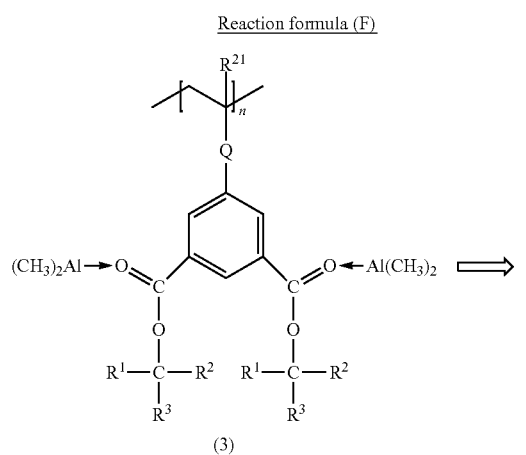

Reaction formula (G)

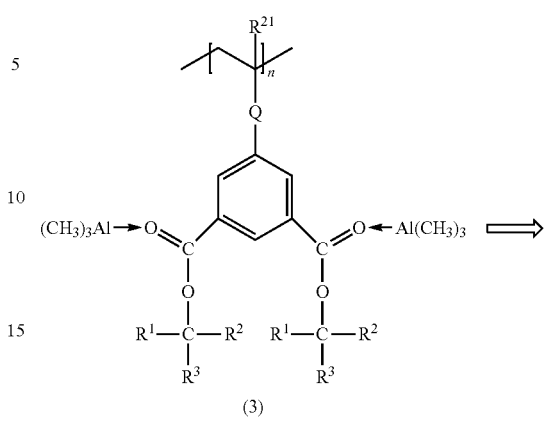

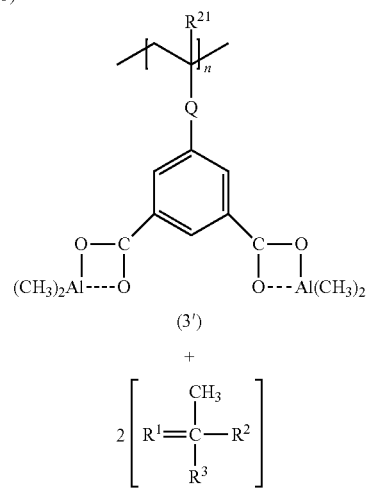

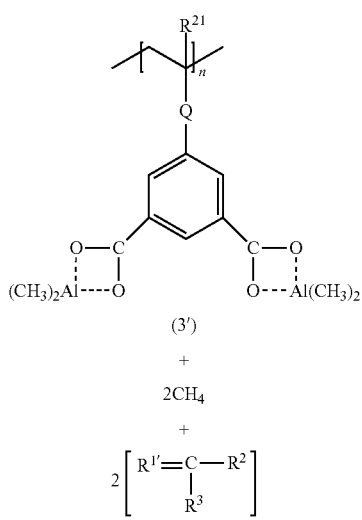

The primary, secondary or tertiary hydrocarbon group ($R^{22}$) ester-bonded to the side-chain terminal of the monomer unit (3) is cleaved under a specific condition even in a case where the metallic compound such as TMA is not adsorbed to the carbonyl group of the monomer unit (3). However, as represented by the reaction formula (F), when the metallic compound such as TMA is coordinated to the carbonyl group of the monomer unit (3), the cleavage of the hydrocarbon group ($R^{22}$ (it is mentioned as $-CR^1R^2R^3$ in the reaction formula (F)) can be achieved under a significantly milder condition than the above-described specific condition. This is a new finding by the present inventors, and it can be said that the metallization of the organic film formed by this pattern forming material allows the metallic compound to be firmly bonded to the organic film and also achieves excellent productivity.

Note that the metallization is performed with respect to the organic film formed by this pattern forming material in the embodiment. The organic film formed by this pattern forming material may be formed of this pattern forming material itself or may be formed by the reaction of the components contained in this pattern forming material as described above.

In this pattern forming material, the organic film formed from the polymer X preferably has at least the structure of the side chain of the monomer unit (3) as it is. This makes it possible that the composite film obtained by metallizing the organic film has, for example, a structure where Al(CH)x (where X is a number of 0 to 2 and is 2 in the monomer unit (3')) being the metallic compound is firmly bonded to two oxygen atoms of the monomer unit (3') as represented by the monomer unit (3').

Besides, as represented by a general formula (5) described below, a structure where, for example, $Al(CH_3)$ derived from TMA ($Al(CH_3)_3$) being the metallic compound is held by two carbonyl groups is also conceivable. In this case, it is considered to form firmer bonding than the case when $Al(CH_3)_2$ is held by one carbonyl group as represented by the general formula (3') in each of the reaction formulas (F) and (G). Note that the number of coordinated carbonyl groups depends on the kind of a metal and steric hindrance of a polymer matrix surrounding the metal. In the general formula (5), $R^{21}$ and Q refer the same as $R^{21}$ and Q in the general formula (3), and n represents the number of repetitions of the monomer unit (3) in the polymer X.

Note that a degree of metallization in the composite film can be verified by measuring an amount of metal held by the metallic compound in the composite film by means of X-ray photoelectron spectroscopy (XPS). The structure where the metal of the metallic compound is bonded to each of two oxygen atoms derived from ester bond which are at the terminal of the side chain of the monomer unit (3) in the organic film can be estimated by means of infrared spectroscopy (IR). That is, IR absorption of carbonyl derived from ester can be detected in the organic film before metallization, whereas, the IR absorption is attenuated after the metallization, having an absorption derived from carbonium ions is newly detected, thereby the metal of the metallic compound is bonded to each of the two oxygen atoms derived from ester bond of the monomer unit (3) in the organic film at the terminal of the side chain.

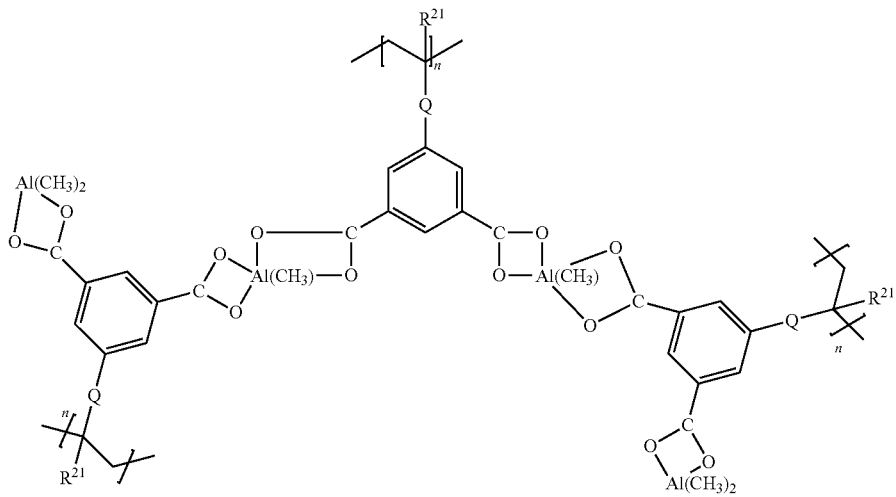

(5)

In the monomer unit (3), α carbon of $R^{22}$ is primary carbon, secondary carbon, or tertiary carbon. $R^{22}$ is explained using a case when $R^{22}$ is represented by $-CR^1R^2R^3$ (where $R^1$, $R^2$ and $R^3$ each independently represent a hydrogen atom or a hydrocarbon group, at least one of these is a hydrocarbon group, and the total number of carbons is 1 to 13) as an example.

When C in $-CR^1R^2R^3$ is a primary carbon, any one of $R^1$, $R^2$ and $R^3$ is a hydrocarbon group, and the remaining two are hydrogen atoms. When C in $-CR^1R^2R^3$ is a secondary carbon, any two of $R^1$, $R^2$ and $R^3$ are hydrocarbon groups, and the remaining one is a hydrogen atom. When C in $-CR^1R^2R^3$ is a tertiary carbon, all of $R^1$, $R^2$, and $R^3$ are hydrocarbon groups. The total number of carbons of $R^1$, $R^2$, and $R^3$ is 1 to 13, and the total number of carbons as $-CR^1R^2R^3$ is 2 to 14.

The present inventors have verified that in a case of a monomer unit where the group ($R^{22}$) ester-bonded to the terminal of the side chain is $CH_3$ in the general formula (3), namely in a case out of a scope of the embodiment, for example, in the metallization using TMA, Al of TMA is adsorbed to the unshared electron pair of =O of the carbonyl group, but a methyl group is difficult to be cleaved from the terminal of the side chain. Accordingly, in such a monomer unit, it is substantially impossible to have a structure of the monomer unit (3') where Al of TMA is bonded to each of two oxygen atoms derived from ester bond.

It is calculated that stabilization energy of Al and O in a state where Al of TMA is coordinated to the unshared electron pair of =O of the carbonyl group is 15 kcal/mol. Meanwhile, in the structure where Al of TMA is bonded to two oxygen atoms derived from ester bond in the monomer unit (3'), it can be calculated that bond energy between Al and the two oxygen atoms is 130 kcal/mol. In the monomer unit (3), a carbon of $R^{22}$, that is, C in $-CR^1R^2R^3$ representing $R^{22}$ is a primary carbon, a secondary carbon or a tertiary carbon which are in order of bond strength.

Furthermore, hydrocarbon obtained by cleavage from the terminal of the side chain of the monomer unit (3) in the event of metallization, for example, $R^{1'}=CR^2R^3$ in the reaction formula (F) is preferably removed away from the composite film. For that purpose, the total number of carbon atoms of $R^1$, $R^2$, and $R^3$ is 1 to 13.

When the composite film obtained by using this pattern forming material is used as an underlayer film of a later-described multilayer mask structure, $-CR^1R^2R^3$ is cleaved from the monomer unit (3) under a relatively mild condition when C in $-CR^1R^2R^3$ is a tertiary carbon. In such a case when another layer is formed on the organic film as the multilayer mask structure and when C in $-CR^1R^2R^3$ is a tertiary carbon, there is a possibility that $-CR^1R^2R^3$ in the organic film is cleaved from the monomer unit when the layer is formed.

When $-CR^1R^2R^3$ in the monomer unit (3) is decomposed to form a carboxylic acid, the formed carboxylic acid may become an acid catalyst and when it is heated, peripheral ester bond may be further hydrolyzed. When C in —$CR^1R^2R^3$ is a primary carbon or a secondary carbon, —$CR^1R^2R^3$ is more difficult to be cleaved compared with the case of the tertiary carbon. Therefore, C in —$CR^1R^2R^3$ is preferably a primary carbon or a secondary carbon depending on a temperature region applied when the underlayer film is formed.

When the α carbon is a tertiary carbon, $R^{22}$ in the monomer unit (3) is a t-butyl group. When the α carbon is a secondary carbon, $R^{22}$ is an isopropyl group or an s-butyl group. When the α carbon is a primary carbon, $R^2$ is an ethyl group, an n-propyl group, an n-butyl group, or an isobutyl group.

Concretely, when C in —$CR^1R^2R^3$ is a tertiary carbon, an example of —$CR^1R^2R^3$ includes the hydrocarbon group where $R^1$, $R^2$, and $R^3$ are each independently, for example, a methyl group, an ethyl group, a propyl group, a butyl group, a pentyl group, a hexyl group, a heptyl group, or an octyl group, and the total number of carbon atoms is 3 to 13. Among these, the t-butyl group where all of $R^1$, $R^2$, and $R^3$ are the methyl groups is preferred as —$CR^1R^2R^3$.

When C in —$CR^1R^2R^3$ is a secondary carbon, an example of —$CR^1R^2R^3$ includes, for example, the hydrocarbon group where when $R^3$ is a hydrogen atom, $R^1$ and $R^2$ are each independently, for example, a methyl group, an ethyl group, a propyl group, a butyl group, a pentyl group, a hexyl group, a heptyl group, an octyl group, or a nonyl group, and the total number of carbon atoms is 2 to 13. Among these, the isopropyl group where both of $R^1$ and $R^2$ are methyl groups, the s-butyl group where $R^1$ and $R^2$ are a methyl group and an ethyl group respectively, a 3-pentyl group where $R^1$ and $R^2$ are both an ethyl group, a 4-heptyl group where $R^1$ and $R^2$ are both a propyl group or a 5-nonyl group where $R^1$ and $R^2$ are both an n-butyl group is preferred as —$CR^1R^2R^3$ (note that $R^3$ is H).

When C in —$CR^1R^2R^3$ is at primary carbon, an example of —$CR^1R^2R^3$ includes the hydrocarbon group where when $R^2$ and $R^3$ are set as the hydrogen atoms, $R^1$ is, for example, a methyl group, a ethyl group, a propyl group, a butyl group, a pentyl group, a hexyl group, a heptyl group, an octyl group, a nonyl group, or a decyl group, and the total number of carbon atoms is 1 to 13. Among these, the ethyl group where $R^1$ is the methyl group, or the propyl group where $R^1$ is the ethyl group is preferred as —$CR^1R^2R^3$ (note that $R^2$ and $R^3$ are H). The benzyl group is also preferred as $R^1$ in —$CR^1R^2R^3$ (note that $R^2$ and $R^3$ are H).

Q in the general formula (3) is a single bond or a hydrocarbon group having 1 to 20 carbon atoms which may include an oxygen atom, a nitrogen atom, or a sulfur atom between carbon-carbon atoms or at a bond terminal, and a halogen atom may also be substituted for a hydrogen atom.

Q preferably is a single bond or an ester bond. When Q is a single bond, the monomer unit (3) is a monomer unit (31) represented by a general formula (31) described below, and when Q is an ester bond, the monomer unit (3) is a monomer unit (32) represented by a general formula (32) described below. Note that in the general formulas (31), (32). $R^{21}$ and $R^{22}$ refer the same as $R^{21}$ and $R^{22}$ in the general formula (3).

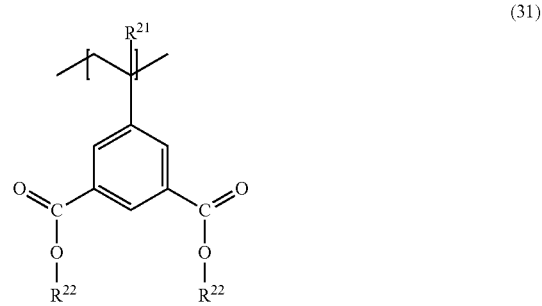

(31)

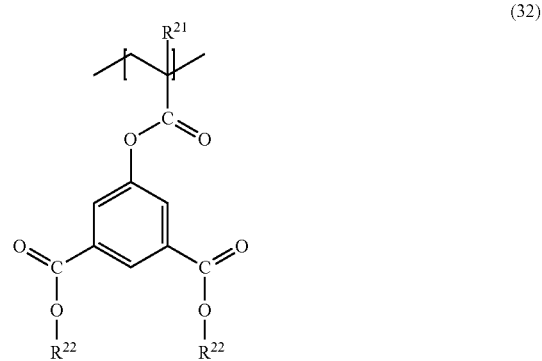

(32)

A compound where $R^{22}$ is an ethyl group, an isopropyl group, or an s-butyl group among constituent monomers of the monomer unit (31) is the compound (1) of the embodiment. A compound where $R^2$ is an ethyl group, an isopropyl group, an s-butyl group, or a t-butyl group among constituent monomers of the monomer unit (32) is the compound (2) of the embodiment. When $R^{22}$ is an ethyl group, an isopropyl group, or an s-butyl group in the monomer unit (3), the α carbon is a primary carbon or a secondary carbon, which is preferred in terms of the above-stated points.

Q in the general formula (3) is a single bond or a hydrocarbon group having 1 to 20 carbon atoms which may include an oxygen atom, a nitrogen atom, or a sulfur atom between the carbon-carbon atoms or at the bond terminal, and a halogen atom may also be substituted for a hydrogen atom. Examples of the halogen atom include F, Cl, and Br. When Q is a single bond, the monomer unit (3) is (meth) acrylate whose constituent monomer is an ester of (meth) acrylic acid.

When Q of the monomer unit (3) is a hydrocarbon group, the hydrocarbon may be a linear, a branched-chain, or a ring, or may be a combination of these. The ring may be a cycloalkyl ring or an aromatic ring, and the aromatic ring is preferred in terms of etch resistance of the obtained composite film. The number of carbon atoms of Q is preferably 1 to 10 when Q is not a ring, and preferably 6 to 18 when Q is a ring. When Q is a hydrocarbon group, an oxygen atom, a nitrogen atom, or a sulfur atom may be included between the carbon-carbon atoms or at the bond terminal, and a halogen atom may also be substituted for the hydrogen atom. Q is preferably a hydrocarbon group having no heteroatom. An example of the case when Q is a hydrocarbon group having no heteroatom includes a 1,4-phenylene group, a 1,4-naphthalene group, a 1,4-anthracene group, or the like.

The polymer X may contain one kind of monomer unit (3), or two or more kinds of monomer units (3). The polymer X may be formed of the monomer unit (3) alone or may be a copolymer of the monomer unit (3) and a monomer unit other than the monomer unit (3). A ratio of the monomer unit (3) in the polymer X is preferably 50 mol % or more, more preferably 80 mol % or more, and further preferably 90 mol % or more with respect to all of the monomer units of the polymer X.

The polymer X has the monomer unit (3), thereby making it possible to achieve both an excellent metallization property in the organic film obtained from this pattern forming material containing the polymer X, and high etch resistance in the obtained mask pattern. In term of the metallization property and etch resistance as stated above, the ratio of the monomer unit (3) in the polymer X is preferably 50 mol % or more, and in case when later-described properties are not considered, the ratio is particularly preferably 100 mol %.

The polymer X can be synthesized from the constituent monomers of the monomer unit by a generally known method such as, for example, bulk polymerization, solution polymerization, emulsion polymerization, or suspension polymerization. The solution polymerization is preferred in terms of redissolution to a solvent after the polymerization as well as eliminating any possible impurities such as an emulsifier and water. When the polymer X is synthesized by solution polymerization, normally, a monomer is dissolved in a polymerization solvent and polymerized in the presence of an initiator. The monomers used for the synthesis of the polymer X include the constituent monomers of the monomer unit (3). As will be described later, when the polymer X includes a monomer unit other than the monomer unit (3), constituent monomers of all the monomer units constituting the polymer X are used in the polymerization reaction. Polymerization conditions such as an amount of the polymerization solvent, the polymerization temperature, and a polymerization time are appropriately selected according to the kind of the monomer, a molecular weight of the polymer X to be synthesized, and the like.

A weight-average molecular weight (Mw) of the polymer X is preferably 1,000 to 1,000,000 [g/mol] (hereinafter, a unit is sometimes omitted), more preferably 2,000 to 1,000,000, and particularly preferably 2,000 to 100,000. The molecular weight (Mw) of the polymer X can be measured by gel permeability chromatography (GPC).

Note that the metallic compound bonded to the organic film may be thereafter appropriately processed to be used as a mask pattern. For example, in a case of $Al(CH_3)_3$ shown in the reaction formula (F), after the metallic compound is bonded to the organic film, aluminum hydroxide, aluminum oxide, or the like may be formed by oxidation treatment. The oxidation treatment is normally performed by using an oxidant such as water, ozone, or oxygen plasma. Note that the oxidation treatment may be performed by moisture in air without any special treatment.

Further, an explanation has been made by exemplifying $Al(CH_3)_3$ as the metallic compound bonded to the organic film, but an Al compound other than $Al(CH_3)_3$ is applicable, and it is possible to obtain similar bonding structures even in metallic compounds of metals other than Al such as, for example, Ti, V, W, Hf, Zr, Ta, and Mo.

The composite film obtained by using this pattern forming material has high etch resistance since the metallic compound is firmly bonded to the organic film. Examples of etching include reactive ion etching (RIE), ion beam etching (IBE), or the like, and it is possible to achieve sufficient resistance even in the IBE where particularly high resistance is required. In order to achieve a pattern having a high aspect ratio with respect to the film to be processed, the multilayer mask structure is sometimes applied in the mask pattern. The composite film formed by using this pattern forming material is suitably used as the underlayer film to be formed between a resist film and the film to be processed when used for the multilayer mask structure.

Conventionally, in the multilayer mask structure targeted for high etch resistance, a carbon layer obtained by chemical vapor deposition (CVD) method has been used as the underlayer film between the resist film and the film to be processed. On the contrary, the composite film formed by this pattern forming material has advantages where materials thereof are inexpensive and a film is easily formed thus allowing a possible substitution for the carbon deposition layer obtained by the very costly CVD method for forming a film.

(Polymer X)

This pattern forming material contains the polymer including the monomer unit (3). In the polymer X, the monomer unit other than the monomer unit (3) may be contained within a range of not impairing the effect of the embodiment in order to impart properties (hereinafter, also mentioned as "other properties".) required in addition to the metallization property and the etch resistance as a material to form the mask pattern.

An example of other properties required for the polymer X includes the property of making the obtained organic film insoluble to an organic solvent. This is a particularly required property when this pattern forming material is applied to the multilayer mask structure. In the multilayer mask structure, the organic film formed by using this pattern forming material as described above is preferably formed as the underlayer film between the resist film and the film to be processed. In this case, normally, other layers constituting the multilayer mask is formed by what is called a wet coating method; a method of coating a material composing the layer dissolved in an organic solvent or the like on top of the organic film. When the organic film formed of the polymer X is soluble to the organic solvent used for the wet coating method, there is a possibility that the organic film is partly dissolved to the organic solvent to form a mixed layer of composing materials of the layer formed on the organic film and the organic film.

The present inventors have overcome the issue by introducing a crosslinkable monomer unit having a crosslinkable functional group at a terminal of a side chain to the polymer X in addition to the monomer unit (3), to suppress the elution of film components in the obtained organic film. This makes it possible that the organic film formed by using the polymer X becomes insoluble to the organic solvent, and when layers on the organic film is formed by the wet coating method, the mixed layer is hardly formed. Hereinafter, the polymer X having the crosslinkable monomer unit in addition to the monomer unit (3) is sometimes mentioned as a crosslinkable polymer X.

The crosslinkable functional group in the crosslinkable monomer unit is not particularly limited as long as it functions as crosslinker, but in terms of stability, a functional group that exhibits a crosslinking function by applying energy from outside, for example by heating or light irradiation, is preferred. Examples of the crosslinkable functional group include a glycidyl group, an oxetanyl group, an amino group, an azido group, a thiol group, a hydroxyl group, a carboxyl group, or the like, and the glycidyl group, the oxetanyl group, the hydroxyl group, the carboxyl group, or the protected carboxyl group is particularly preferred front the viewpoints where a structure after crosslinkage is inert to the metallic compound, as well as energy required for a crosslinking reaction is relatively low.

An example of a constituent monomer of the crosslinkable monomer unit includes a monomer where a monovalent organic group having a crosslinkable functional group at a terminal is bonded to any carbon atom of an ethylene group. Concretely, an example of the crosslinkable monomer unit includes a monomer unit (4) represented by a general formula (4) described below.

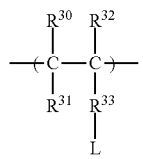
(4)

In the general formula (4), $R^{30}$, $R^{31}$, and $R^{32}$ are each independently a hydrogen atom or a hydrocarbon group having 1 to 10 carbon atoms, and $R^{33}$ is a single bond or a hydrocarbon group having 1 to 20 carbon atoms which may include an oxygen atom, a nitrogen atom, or an ester bond between carbon-carbon atoms or at a bond terminal, and L is a crosslinkable functional group.

As a constituent monomer of the crosslinkable monomer unit, (meth)acrylate where a compound having a crosslinkable functional group at a terminal is ester-bonded to (meth)acrylic acid or a styrene derivative where a compound having a crosslinkable functional group at a terminal is substituted is preferred.

An example of (meth)acrylate having the glycidyl group among (meth)acrylates to be the constituent monomer of the crosslinkable monomer unit concretely includes a compound represented by a general formula L1 described below.

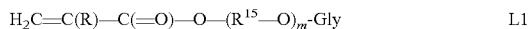
L1

In the general formula L1, R is a hydrogen atom or a methyl group, and Gly is the glycidyl group, m is 0 to 3, and $R^{15}$ is an alkylene group having 1 to 10 carbon atoms. An example of (meth)acrylate represented by L1 concretely includes glycidyl (meth)acrylate represented by a general formula L1-1 described below. In each of the following general formulas, R is a hydrogen atom or a methyl group.

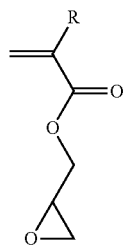
L1-1

Concretely, an example of (meth)acrylate having the oxetanyl group among (meth)acrylates to be the constituent monomer of the crosslinkable monomer unit includes (3-ethyl-3-oxetanyl)methyl(meth)acrylate represented by a general formula L2-1 described below. In the following general formula, R is a hydrogen atom or a methyl group.

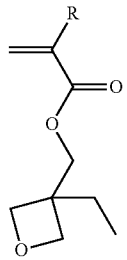
L2-1

Concretely, an example of the styrene derivative having the glycidyl group among styrene derivatives to be the constituent monomer of the crosslinkable monomer unit includes a compound represented by a general formula L3 described below.

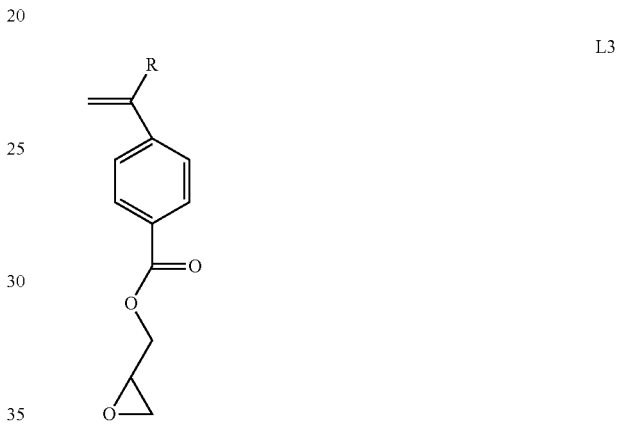
L3

A copolymer of the monomer unit (3) and the crosslinkable monomer unit constituting the polymer X preferably has randomness, and it is sufficient that a combination of the monomer unit (3) and the crosslinkable monomer unit is determined from the above viewpoint.

When the polymer X contained by this pattern forming material contains the crosslinkable monomer unit, the polymer X may contain only one kind of crosslinkable monomer unit, or may contain two or more kinds of crosslinkable monomer units. When the polymer X contains one kind of monomer unit (3) and two or more kinds of crosslinkable monomer units, the polymer X may be a mixture of two or more kinds of copolymers each including the monomer unit (3) and each of the crosslinkable monomer units or may be one kind of copolymer including one kind of monomer unit (3) and two or more kinds of crosslinkable monomer units.

When the polymer X contains two or more kinds of monomer units (3) and one kind of crosslinkable monomer unit, the polymer X may be a mixture of two or more kinds of copolymers each including the crosslinkable monomer unit and each of the monomer units (3), or may be one kind of copolymer including two or more kinds of monomer units (3) and one kind of crosslinkable monomer unit.

When the polymer X contains the monomer unit (3) and the crosslinkable monomer unit, the crosslinkable functional groups of the crosslinkable monomer units included in different polymer chains react with each other to be bonded, resulting in that the respective main chains of a plurality of polymers are crosslinked to make it difficult to dissolve the polymer regardless of whether the polymer X is a mixture of two or more kinds of copolymers or is constituted by one kind of copolymer as described above. Note that the reaction of the crosslinkable functional groups is preferably performed by, for example, heating, light irradiation, or the like after the organic film is formed.

A ratio of the crosslinkable monomer unit in the polymer X is preferably 0.5 mol % or more and less than 20 mol %, more preferably 1 mol % or more and less than 10 mol %, and further preferably 2 mol % or more and less than 10 mol % to all of the monomer units constituting the polymer X.

When the ratio of the crosslinkable monomer unit is less than 0.5 mol % to all of the monomer units, the crosslinking in the polymer X cannot be sufficiently achieved allowing the polymer to dissolve into a solvent, resulting in a possibility that the component of the organic film is eluted to a wet coating solution used for forming an upper layer on the organic film. When the ratio of the crosslinkable monomer unit is 20 mol % or more to all of the monomer units, there is a possibility that high crosslink density causes suppression of diffusion of the metallic compound into the organic film which prevents the organic film from metallization deep throughout its thickness Hereinafter, the crosslinkable polymer X will be explained by exemplifying a case where the crosslinkable monomer unit is the monomer unit L1-1. The following explanation is applied to the crosslinkable polymer X even when the crosslinkable monomer unit is other crosslinkable monomer units than the monomer unit L1-1.

A chemical structural formula X11 described below represents a chemical structural formula of the polymer X constituted by combining the monomer unit (3) and the monomer unit L1-1. The polymer represented by the chemical structural formula X11 is hereinafter mentioned as a polymer X11. Hereinafter, other polymers are also denoted similarly. In the chemical structural formula X11, $R^{21}$, $R^{22}$, and Q refer the same as $R^{21}$, $R^{22}$, and Q in the general formula (3), and R is a hydrogen atom or a methyl group.

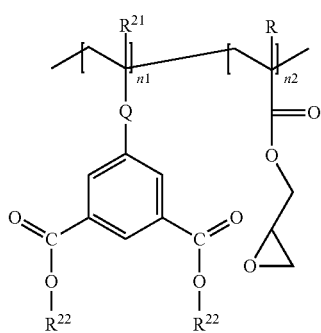

X11

The polymer X11 is constituted of the monomer unit (3) and the monomer unit L1-1. A molar ratio of the monomer unit L1-1 to all the monomer units in the polymer X11 is represented by n2, and a molar ratio of the monomer unit (3) to all the monomer units in the polymer X11 is represented by n1. A sum of n1 and n2 is 100 mol % in the polymer X11. Note that in the polymer X11, the monomer unit (3) and the monomer unit L1-1 may be alternately present, or may be randomly present. The respective monomer units are preferably uniformly present according to content ratios of the respective monomer units.

When the polymer X contained by this pattern forming material is the crosslinkable polymer X and constituted of only the polymer X11, n2 in the polymer X11 is preferably 0.5 mol % or more and less than 20 mol %, more preferably 1 mol % or more and less than 10 mol %, and further more preferably 2 mol % or more and less than 10 mol % by the similar reason to the above explanation. Besides, n1 is preferably more than 80 mol % and 99.5 mol % or less, more preferably more than 90 mol % and 99 mol % or less, and further more preferably more than 90 mol % and 98 mol % or less.

The crosslinkable polymer X may be a mixture of the polymer X11 and the other crosslinkable polymer X. When the crosslinkable polymer X is the mixture of the polymer X11 and the other crosslinkable polymer X, content ratios of the monomer unit (3) and the crosslinkable monomer unit in each crosslinkable polymer does not necessarily fall within the above-described ranges. The content ratios of the monomer unit (3) and the crosslinkable monomer unit preferably fall within the above-described range as the entire mixture.

Adjustment of ratios of the respective monomer units in the crosslinkable polymer X can be performed by adjusting ratios of monomers added at a time of polymerization. A molecular weight (Mw) of the crosslinkable polymer X is preferably 1,000 to 100,000,000, and more preferably 2,000 to 100,000.

Conditions when the crosslinkable polymers X are crosslinked depend on the kind of crosslinkable functional group in by the crosslinkable monomer unit. For example, when the crosslinkable functional group is the glycidyl group or the oxetanyl group, the crosslinking is achieved by opening an epoxy ring or an oxetane ring. Accordingly, the polymers X are crosslinked by heating or light irradiation under the conditions that the epoxy ring or the oxetane ring is opened. Note that when the crosslinkable polymer X is crosslinked, a curing agent may be used.

The curing agent has a reactivity with the crosslinkable functional group and allows the crosslinkable functional groups to be bonded to each other by the curing agent. The curing agent promotes a crosslinking reaction and makes the crosslinking of the polymers X easy. Accordingly, a suitable curing agent depends on the kind of the crosslinkable monomer unit. For example, when the crosslinkable functional group held by the crosslinkable monomer unit is a glycidyl group, an amine compound, a compound having an acid anhydride structure, a compound having a carboxylic acid, or a compound having a hydroxyl group can be suitably used as the curing agent.

The amine compound has a plurality of primary amines or secondary amines in a structure. Examples of the amine compound usable for the curing agent include, for example, ethylenediamine, trimethylenediamine, tetramethylenediamine, pentamethylenediamine, hexamethylenediamine, heptamethylenediamine, octamethylenediamine, nonamethylenediamine, decamethylenediamine, diethylenetriamine, triethylenetetramine, tetraethylenepentamine, pentaethylenehexamine, 1,2-diaminocyclohexane, 1,3-diaminocyclohexane, 1,4-diaminocyclohexane, o-phenylenediamine, m-phenylenediamine, p-phenylenediamine, m-xylenediamine, p-xylenediamine, isophorondiamine, 4,4'-methylenedianiline, diaminodiphenylsulfone, diaminodiphenyl ether, or the like.

Examples of the compound having the acid anhydride structure usable for the curing agent include, for example, hexahydrophthalic anhydride, 4-methylhexahydrophthalic anhydride, succinic anhydride, itaconic anhydride, dodecenylsuccinic anhydride, or the like.

Examples of the compound having the carboxylic acid usable for the curing agent include, for example, hexahydrophthalic acid, 4-methylhexahydrophthalic acid, succinic acid, itaconic acid, dodecenylsuccinic acid, citric acid, terephthalic acid, or the like.

The compound having a hydroxyl group includes a plurality of hydroxyl groups in a structure. Examples of the compound having a hydroxyl group usable for the curing agent include, for example, polyphenol, 1,4-benzenediol, 1,3-benzenediol, 1,2-benzenediol, ethylene glycol, or the like.

A curing promotor having tertiary amine may be added in order to enhance the reactivity of the curing agents other than the curing agent of the amine compound. Examples of such a curing accelerator include, for example, cyandiamide, 1,8-diazabicyclo(5,4,0)-undecene-7, 1,5-diazabicyclo (4.3.0)-nonene-5, tris(dimethylaminomethyl)phenol, ethylene glycol, or the like.

When this pattern forming material contains a curing agent together with the crosslinkable polymer X, an amount of the curing agent is preferably an amount where a ratio of a reactive group to the crosslinkable functional group in the curing agent is 0.01 to 1 mol with respect to 1 mol of the crosslinkable functional group in the crosslinkable polymer X.

The polymer X contained by this pattern forming material may further include another monomer unit (hereinafter, mentioned as "an alternative monomer unit") other than the monomer unit (3) and the crosslinkable monomer unit as necessary. In the polymer X, having the alternative monomer unit makes it possible to adjust solubility of the polymer X to an organic solvent, film formability when coating a film, a glass transition temperature of the film after coating the film, heat resistance, and the like.

Examples of a monomer constituting the alternative monomer unit include, for example, styrene, 1-vinylnaphthalene, 2-vinylnaphthalene, 9-vinylanthracene, vinylbenzophenone, hydroxystyrene methyl (meth)acrylate, (meth) acrylic acid, methyl 4-vinyl benzonate, 4-vinyl benzoic acid, a monomer represented by a general formula (6) described below, or the like. The alternative monomer unit can be constituted of at least any one of these monomers.

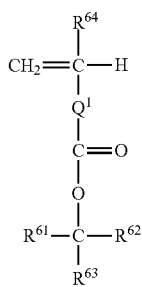

(6)

In the general formula (6), $R^{61}$, $R^{62}$, and $R^{63}$ each independently represent a hydrogen atom or a hydrocarbon group which may include an oxygen atom, at least one of these is the hydrocarbon group, the total number of carbons of these is 1 to 13, and these may form a ring by being bonded to each other. $R^4$ is a hydrogen atom or a methyl group. $Q^1$ is a single bond or a hydrocarbon group having 1 to 20 carbon atoms which may contain an oxygen atom, a nitrogen atom, or a sulfur atom between carbon-carbon atoms or at a bond terminal, and a halogen atom may be substituted for a hydrogen atom.

A ratio of the alternative monomer unit is preferably 50 mol % or less, more preferably 10 mol % or less, and further preferably 1 mol % or less to all the monomer units constituting the polymer X. Setting the ratio of the alternative monomer unit to 50 mol % or less makes it possible to keep the content of the monomer unit (3) in the organic film high, and firmly bond a larger amount of the metallic compound in the organic film.

This pattern forming material may contain a component other than the polymer X as necessary within a range of not impairing the effect of this embodiment in addition to the polymer X. Examples of the component other than the polymer X typically include the above-described curing agent and curing promotor. Examples of a component other than the curing agent and the curing promotor include a thermal acid generator, a photoacid generator, or the like. A content of the component other than the polymer X in this pattern forming material can be appropriately selected according to each of the components. For example, the content of the curing agent is as explained above. The content of the component excluding the polymer X other than the curing agent is preferably 1 wt % or less, and more preferably 0.1 wt % or less to the total amount of the pattern forming material.

A method of forming the organic film by using this pattern forming material may be a dry coating method or a wet coating method. When the organic film is formed by the dry coating method, the organic film can be formed for example, by a vapor disposition method by using this pattern forming material itself. When the organic film is formed by the wet coating method, coating a composition including this pattern forming material in an organic solvent and drying on the film that is to be processed to form the organic film is preferred.

(Embodiment of Composition for Pattern Formation)

A composition for pattern formation (hereinafter, also simply mentioned as a "composition".) of the embodiment is a composition where an organic film is formed by using a pattern forming material to be patterned on a film to be processed of a substrate having the film to be processed, and thereafter a composite film obtained by infiltrating a metallic compound into the organic film is used as a mask pattern when the film that is to be processed is processed, and which includes the pattern forming material for forming the organic film, and the composition contains the pattern forming material containing the polymer including the monomer unit (3) represented by the above-described general formula (3) and the organic solvent capable of dissolving the pattern forming material.

This pattern forming material can be used as the pattern forming material in the composition of the embodiment. The composition of the embodiment can be used for a similar use to that of the one explained above in this pattern forming material. The organic solvent in the composition of the embodiment is not particularly limited as long as it is an organic solvent dissolving this pattern forming material, particularly the polymer X contained by this pattern forming material.

Examples of the organic solvent dissolving the polymer X include aromatic hydrocarbons such as toluene, xylene, and mesitylene, ketones such as cyclohexanone, acetone, ethyl methyl ketone, and methyl isobutyl ketone, or cellosolves such as methyl cellosolve, methyl cellosolve acetate, ethyl cellosolve acetate, butyl cellosolve acetate, and propylene glycol monomethyl ether acetate (PGMEA). Among the solvents described the cellosolves are preferred. The organic solvent can be used by combining two or more kinds if necessary.

A content of the pattern forming material in the composition of the embodiment is preferably 1 to 30 wt %, more preferably t to 20 wt %, and further preferably 1 to 15 wt % to the entire composition. A content of the organic solvent in the composition of the embodiment is preferably 70 to 99 wt %, more preferably 80 to 99 wt %, and further preferably 85 to 99 wt % to the entire composition. The content of each of the pattern forming material and the organic solvent in the composition of the embodiment falls within the above-described range, thereby making it possible to form the organic film well by the wet coating method onto the film that is to be processed.

A normal method is applicable as a method of coating the composition of the embodiment on the film to be processed by the wet coating method. Concretely, spin coating or dip coating is preferred. The organic film can be formed by removing the organic solvent from a coated film of the composition during drying process. When the polymer X is the crosslinkable polymer X, crosslinking treatment is performed to cause crosslinking, for example, by heating or light irradiation, according to the crosslinkable polymer X used at a time of organic film formation.

Here, when the organic film is formed by the composition of the embodiment, the organic film is preferably formed under a condition where $R^{22}$ is not cleaved from the monomer unit (3). If $R^{22}$ is cleaved from the monomer unit (3) when the organic film is formed, there is a possibility that uniform metallization does not occur throughout the film thickness at the metallization procedure that is later to be performed. It is highly likely that a firm bond between the organic film and the metallic compound cannot be achieved.

(Embodiment of Pattern Forming Method and Manufacturing Method of Semiconductor Device)

A pattern forming method of the embodiment has processes of (A1) to (C) described below.
(A1) a process of forming an organic film on a substrate by using a pattern forming material containing a polymer including the monomer unit (3).
(B) a process of patterning the organic film obtained by (A1).
(C) a process of forming a composite film by infiltrating a metallic compound into the patterned organic film to obtain a mask pattern formed of the composite film.

A manufacturing method of a semiconductor device of the embodiment has processes of (A) to (D) described below.
(A) a process of forming an organic film on a film to be processed which is provided with a substrate by using a pattern forming material containing a polymer including the monomer unit (3).
(B) a process of patterning the organic film obtained by (A).
(C) a process of forming a composite film by infiltrating a metallic compound into the patterned organic film to obtain a mask pattern formed of the composite film.
(D) a process of processing the film that is to be processed by using the mask pattern.

This pattern forming material explained above is applicable as a pattern forming material to be used in this pattern forming method and the manufacturing method of the semiconductor device of the embodiment.

Hereinafter, the manufacturing method of the semiconductor device of the embodiment will be explained by using FIG. 1A to FIG. 1E. Here, the processes of (A1), (B), and (C) in the pattern forming method of the embodiment correspond to the processes of (A), (B), and (C) in the manufacturing method of the semiconductor device of the embodiment, respectively. Accordingly, to each of the processes of (A1), (B), and (C) in the pattern forming method of the embodiment, a concrete method of each of the processes of (A), (B), and (C) in the manufacturing method of the semiconductor device described below can be similarly applied.

FIG. 1A to FIG. 1E are cross sectional views each illustrating one process of the manufacturing method of the semiconductor device according to the embodiment. In the manufacturing method of the semiconductor device of the embodiment, the processes progress in order of FIG. 1A to FIG. 1E.

FIG. 1A is a cross sectional view schematically illustrating the process (A), namely, the process where the organic film is formed on the film on the substrate that is to be processed. The film on the substrate is to be processed by the pattern forming material. In this embodiment, an organic film 3 is formed from the pattern forming material in order to process a film to be processed 2 formed on a semiconductor substrate 1.

In the process (A), first, the semiconductor substrate 1 on which the film to be processed 2 has been formed is prepared. The film to be processed 2 may be a single layer film of a silicon oxide film or the like, or may be a multilayer film composing a three-dimensional memory cell array such as a NAND-type flash memory, or the like. In an example illustrated in FIG. 1A, the film to be processed 2 is a multilayer film where nitride films 21 and oxide films 22 are alternately layered.

Here, in the pattern forming method of the embodiment, the semiconductor substrate 1 may have the film to be processed 2, but the film to be processed 2 is not essential. Further, in the pattern forming method, a substrate of glass, quartz, mica, or the like can be used in place of the semiconductor substrate 1.

This pattern forming material is coated on the film to be processed 2 of the semiconductor substrate 1. In a case of the dry coating method such as vapor deposition, for example, this pattern forming material itself is coated. In a case of the wet coating method such as spin coating or dip coating, the composition of the embodiment is coated. Next, drying for removal of the organic solvent, and heating or light irradiation for crosslinking are performed if necessary to form the organic film 3 on the film to be processed 2.

The drying is performed in the case of the wet coating method. The crosslinking is performed in a case where the polymer X contained by this pattern forming material is the crosslinkable polymer X. The crosslinking is achieved by bonding crosslinkable functional groups between different polymers to each other. When the curing agent or the like is added, such a bond of crosslinkable functional groups is performed through molecules of the curing agent. Heating or light irradiation may be performed in order to promote a crosslinking reaction.

When the crosslinking is performed upon heating, heating temperature depends on the kinds of the crosslinkable functional group in the crosslinkable monomer unit and the curing agent. The heating temperature is preferably about 120° C. or higher, more preferably 160° C. or higher, and further preferably 200° C. or higher. Note that, as mentioned above, the heating is preferably performed at a temperature where $R^{22}$ is not cleaved from the monomer unit (3). Besides, the heating is preferably performed at a temperature where decomposition of a polymer main chain is eliminated.

For example, when the α carbon of $R^{22}$ in the monomer unit (3) is the tertiary carbon, the heating temperature is preferably about 250° C. or lower, and more preferably 200° C. or lower. When the α carbon of $R^{22}$ is the secondary carbon, the heating temperature is preferably about 300° C.

or lower, and more preferably 250° C. or lower. When the α carbon of $R^2$ is the primary carbon, the heating temperature is preferably about 350° C. or lower, and more preferably 300° C. or lower. Note that in a case of the wet coating method, normally, the drying, namely the removal of the organic solvent contained in the composition of the embodiment is performed collectively by this heating. Thus, the organic film 3 formed of this pattern forming material, or obtained by crosslinking the polymers X in this pattern forming material can be obtained.

Figure 1B:
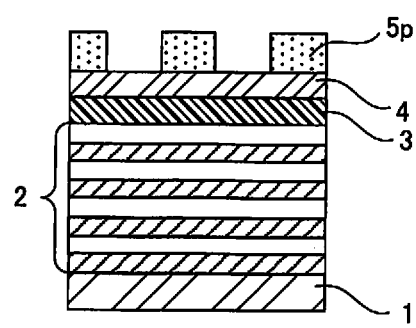
Figure 1C:
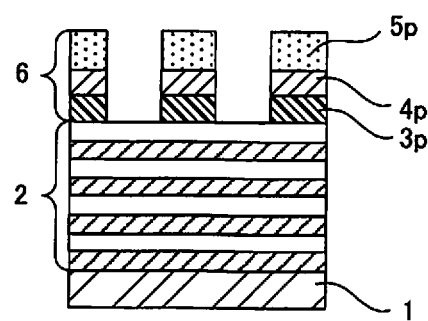

FIG. 1B and FIG. 1C are sectional views each schematically illustrating the process (B), namely, the process where the organic film 3 obtained in the process (A) is patterned. The organic film 3 functions as an underlayer of a multilayer mask structure 6 as illustrated in FIG. 1B and FIG. 1C. FIG. 1B illustrates a state where a silicon oxide film 4 is formed on the organic film 3 as a functional film that is to be patterned and a resist pattern 5p is formed thereon.

The silicon oxide film 4 is formed by, for example, beating a SOG (spin on glass) film formed on the organic film 3 by the following method at a predetermined temperature, for example, between 150° C. and 300° C. Similarly to the above, the heating is preferably performed at the temperature where Rr is not cleaved from the monomer unit (3). The SOG film is formed by spin-coating a wet coating solution where components of the SOG film have been dissolved in an organic solvent on the organic film 3.

Although unillustrated, antireflection film may be formed on the silicon oxide film 4. The antireflection film allows precision exposure by preventing reflection from an underlayer when a resist film which is formed by the following treatment is patterned. A material such as a novolac resin, a phenol resin, or polyhydroxystyrene can be used as the antireflection film.

Next, the resist film is formed on the silicon oxide film 4, and the resist film is formed into the resist pattern 5p by using a lithography technology, an imprint technology, or the like. In the imprint technology, the resist pattern 5p is formed by dropping a resist on the silicon oxide film 4, pressing a template where a fine pattern has been formed to the resist film, and curing the resist film by irradiation with ultraviolet rays.

FIG. 1C is a cross sectional view illustrating a state after etching the silicon oxide film 4 using the resist pattern 5p as a mask, to form a silicon oxide pattern 4p, and further etching the organic film 3 using the resist pattern 5p and the silicon oxide pattern 4p as masks, to form an organic film pattern 3p. The etching of the silicon oxide film 4 is performed by using fluorine-based gas (F-based gas), and the etching of the organic film 3 is performed by using oxygen-based gas ($O_2$-based gas). As illustrated in FIG. 1C, a structure where the organic film pattern 3p, the silicon oxide pattern 4p, and the resist pattern 5p are layered in this order is one example of the multilayer mask structure 6.

When the antireflection film is formed on the silicon oxide film 4, the antireflection film is patterned before the etching of the silicon oxide film 4. Note that after the formation of the silicon oxide pattern 4p, a film thickness of the resist pattern 5p may be adjusted so that the resist pattern 5p is simultaneously removed. Further, after the formation of the organic film pattern 3p, a film thickness of the silicon oxide film pattern 4p may be adjusted so that the silicon oxide pattern 4p is simultaneously removed.

When the organic film pattern 3p is formed based on the multilayer mask structure 6 as presented in this embodiment, the silicon oxide pattern 4p and the resist pattern 5p being upper layers of the organic film pattern 3p may be removed before the process where the composite film is formed by infiltrating the metallic compound into the patterned organic film (organic film pattern 3p) to obtain a mask pattern formed of the composite film, which is the process (C).

Figure 1D:
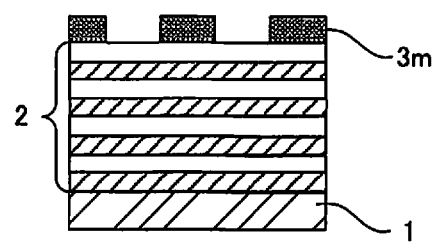

FIG. 1D is a cross sectional view illustrating a state after the process (C), and the organic film pattern 3p illustrated in FIG. 1C is metallized to become a mask pattern 3m on the film to be processed 2 on the semiconductor substrate 1. Note that in the process from the formation of the organic film 3 to the formation of the organic film pattern 3p, the condition is adjusted so that $R^{22}$ in the monomer unit (3) derived from the polymer X at the terminal of the side chain is not cleaved. The metallization of the organic film pattern 3p formed in this manner is performed, for example, as stated below.

A multilayer body having the film to be processed 2 and the organic film pattern 3p on the semiconductor substrate 1 in that order is carried in a vacuum device, and the organic film pattern 3p is exposed to gas or liquid of the metallic compound such as TMA as a metal-containing fluid. Molecules of the metallic compound are adsorbed to the carbonyl group of the monomer unit (3) in the polymer of the organic film pattern 3p and $R^{22}$ is cleaved as represented in the above-described reaction formula (F). Then, for example, as represented by the monomer unit (3') in the reaction formula (F), a structure where the metallic compound ($Al(CH_3)_x$) is firmly bonded to each of two oxygen atoms of the organic film is formed.

In order to firmly bind the metallic compound to the organic film pattern 3p as described above, exposure treatment of the metallic compound to the organic film pattern 3p is preferably performed under heating. A heating temperature is appropriately selected according to a kind of the metallic compound and a kind of the monomer unit (3), particularly the kind of $R^{22}$. For example, when the metallic compound is TMA and the α carbon of $R^{22}$ of the monomer unit (3) is the tertiary carbon, setting the heating temperature at 50° C. or higher, preferably 100° C. or higher likely enables $R^{22}$ to decompose and allows TMA to firmly bond to the organic film.

When the metallic compound is TMA, and the α carbon of $R^{22}$ of the monomer unit (3) is the secondary carbon, setting the heating temperature at 80° C. or higher, preferably 100° C. or higher likely enables $R^{22}$ to decompose and allows TMA to firmly bond to the organic film. Moreover, when the metallic compound is TMA, and the a carbon of $R^{22}$ of the monomer unit (3) is the primary carbon, setting the heating temperature at 100° C. or higher, preferably 120° C. or higher likely enables $R^{22}$ to decompose and allows TMA to firmly bond to the organic film. An upper limit of the heating temperature in this case is preferably set to 400° C. in terms of, for example, preventing a main chain of the polymer of the organic film pattern 3p from being decomposed.

A metallic compound that is used in a CVD method or an atomic layer deposition (ALD) method can be used as the metallic compound without any particular limitation.

Examples of metals included in the metallic compound include aluminum, titanium, tungsten, vanadium, hafnium, zirconium, tantalum, molybdenum, and so on. Among these organometallic compounds or halides, ones having a sufficiently small ligand are usable as the metallic compound.

Concretely, the usable metallic compound can include at least any one of $ACl_3$, $TiCl_4$, $WCl_6$, $VCl_4$, $HfCl_4$, $ZrCl_4$, TMA, and the like. TMA is preferred in this embodiment.

According to the above, the polymer constituting the organic film pattern 3p is metallized to form the mask pattern 3m formed of the composite film of the organic film and the metallic compound. Note that after bonding the metallic compound in the organic film pattern 3p, the resultant may be subjected to oxidation treatment such as exposure to a water vapor atmosphere. For example, when TMA is used as the metallic compound in the above, TMA becomes aluminum hydroxide or the like due to the oxidation treatment. The oxidation treatment is performed normally by using an oxidant such as water, ozone, or oxygen plasma. Note that the oxidation treatment is sometimes performed naturally by moisture in air without any special treatment.

Figure 1E:
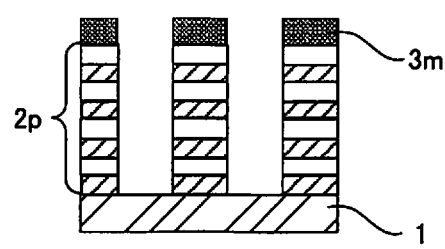

Next, the film to be processed 2 is etched by RIE, IBE, or the like while using the mask pattern 3m as a mask as illustrated in FIG. 1E, to form a patterned film to be processed 2p. This enables to form the film to be processed 2p provided with a processing shape having a high aspect ratio.

After that, for example, a memory cell array is formed by using an already-known method. For example, it is assumed that a hole pattern is formed on a layered film by the above-described process. A memory structure can be formed by embedding a block layer, a charge storage layer, a tunnel layer, a channel layer, and a core layer in such a hole. Thereafter, only nitride films are removed in the layered film through slits formed aside from the hole pattern having the memory structure, and conductive films are alternatively embedded. This causes a layered film where insulating films (oxide films) and the conductive films are alternately layered. The conductive films in the layered film can be made to function as word lines.

Since this pattern forming material contains the polymer having the monomer unit (3) represented by the general formula (3), the metallic compound can be firmly bonded to the organic film obtained by using this owing to the metallization. Then, the composite film obtained by the metallization has high etch resistance and particularly high IBE resistance. This makes it possible to obtain the mask pattern 3m with high etch resistance and makes it possible to impart a processing shape having a high aspect ratio to the film that is to be processed by using this pattern forming material.

When the polymer contained in this pattern forming material is the crosslinkable polymer including the crosslinkable monomer unit having a crosslinkable functional group at a terminal of a side chain in addition to the monomer unit (3), crosslinking the polymers makes it possible to make that the obtained organic film insoluble to organic solvent. This allows to form an upper layer film such as the functional film or a precursor film thereof by coating or dropping of the solution, or the like. It is possible to suppress mixing of the organic film with the upper layer film or the precursor film thereof. For example, an SOC (spin on carbon) film, a TEOS (tetraethyl orthosilicate) film, a resist film, or the like as the upper layer film or the precursor film thereof in addition to the above-mentioned SOG film, which dramatically increases flexibility of design of the multilayer mask structure.

According to this pattern forming material, the organic film can be formed by the method such as spin coating, dip coating, or vapor deposition. For example, though a carbon deposition layer obtained by using the conventionally used CVD method requires a long time for film formation, the organic film to be the composite film provided with high etch resistance can be formed simply in a short time according to this pattern forming material. The method where the organic film is formed into the composite film by the metallization is also a simple and economical method. Note that in a case of the wet coating method such as spin coating or dip coating, the composition of the embodiment can be used.

Note that in the above-mentioned embodiment, the example of metallizing the organic film pattern 3p mainly in a gas phase is given, but it is not limited thereto. The organic film pattern 3p may be metallized in a liquid phase.

Further, in the above-mentioned embodiment, mainly, the structure having the organic film 3, the silicon oxide film 4, and the resist pattern 5p is presented as the multilayer mask structure, but it is not limited thereto. Various configurations can be employed by inserting various films in addition to the above-described ones or reducing some of the above-described films as the multilayer mask structure.

In the above-mentioned embodiment, the mask pattern 3m is formed on the semiconductor substrate 1, but it is not limited thereto. The mask pattern can be formed on a substrate of glass, quartz, mica, or the like in addition to the semiconductor substrate of silicon or the like.

EXAMPLES

The present invention will be explained in further detail by using examples below, but the present invention is not limited to these examples.

Examples 1 to 3

A compound where $R^5$ was a hydrogen atom, and each of $R^{22}$ was an ethyl group, an isopropyl group, or an s-butyl group in the compound (1) was synthesized according to the reaction formula (1).

Dicarboxylic acid in 5-methylbenzene-1,3-dicarboxylic acid was reacted with thionyl chloride, and then methanol was reacted in the presence of triethylamine to protect the carboxylic acid. After that, the methyl group was brominated with N-bromosuccinimide (NBS), reacted by triphenylphosphine, before a vinyl group was formed by formaldehyde in the presence of sodium hydroxide. At the same time, deprotection of the dicarboxylic acid protected by the methyl group was performed, to obtain 5-vinylbenzene-1,3-dicarboxylic acid.

The obtained 5-vinylbenzene-1,3-dicarboxylic acid was dissolved in DMF (N,N-dimethyl formaldehyde) together with N, N'-carbonyldiimidazole in a small excess. Alcohol was reacted at room temperature in the presence of 1,8-diazabicyclo[5.4.0]-7-undecen (DBU) to obtain 5-vinyl-1,3-bisalkylisophthalic acid.

In Example 1, when 5-vinyl-1,3-bis(ethyl)isophthalic acid (a compound where $R^5$ is a hydrogen atom, and each of $R^{22}$ is an ethyl group in the general formula (1), hereinafter, denoted as "M(1)Et".) was obtained, ethanol was used as the alcohol.

In Example 2, when 5-vinyl-1,3-bis(isopropyl)isophthalic acid (a compound where $R^1$ is a hydrogen atom, and each of $R^{22}$ is an isopropyl group in the general formula (1), hereinafter, denoted as "M(1)iP".) was obtained, isopropyl alcohol was used as the alcohol.

In Example 3, when 5-vinyl-1,3-bis(s-butyl)isophthalic acid (a compound where $R^5$ is a hydrogen atom, and each of $R^{22}$ is an s-butyl group in the general formula (1), hereinafter, denoted as "M(1)sB".) was obtained, s-butyl alcohol was used as the alcohol.

Examples 4 to 8

A compound where $R^{11}$ was a methyl group and each of $R^{12}$ was a methyl group, an ethyl group, an isopropyl group, an s-butyl group, or a t-butyl group in the compound (2) was synthesized according to the reaction formula (2).

In Example 4, methacrylic acid chloride was reacted with dimethyl-5-hydroxy-isophthalate in the presence of trimethylamine to obtain dimethyl methacrylate isophthalate (hereinafter, denoted as "M(2)Me".).

Diethyl methacrylate isophthalate (hereinafter, denoted as "M(2)Et".; Example 5), diisopropyl methacrylate isophthalate (hereinafter, denoted as "M(2)iP".; Example 6), di-s-butyl methacrylate isophthalate (hereinafter, denoted as "M(2)sB".; Example 7), and di-t-butyl methacrylate isophthalate (hereinafter, denoted as "M(2)tB".; Example 8) were similarly obtained by carrying out similar reactions with diethyl 5-hydroxy isophthalate, diisopropyl 5-hydroxy isophthalate, di-s-butyl 5-hydroxy isophthalate, and di-t-butyl 5-hydroxy isophthalate.

Examples 11 to 161

First, a polymer X constituted of only the monomer unit (3) was synthesized according to a method described below. A composition for pattern formation was prepared by using a pattern forming material containing the obtained polymer X and an organic solvent to be evaluated.

Ten mmol of the constituent monomer of the monomer unit (3) and 0.1 mmol of azobisisobutyronitrile (AIBN) as an initiator were put in a 100 cc round-bottomed flask, and approximately 5 mL of toluene was added as a solvent. After air in the flask was removed by nitrogen, polymerization was carried out under the temperature of 100° C. for eight hours. After the reaction was completed, the flask was made open to the atmosphere to terminate the polymerization, and then a reaction solution was dropped in a large excess of methanol to purify a polymer component by reprecipitation. The obtained solid was filtered off, and the solid was dried in a vacuum for several days to obtain the desired polymer X. Table 1 presents a relationship between an abbreviation of the polymer X and the monomer unit (3).

TABLE 1

| Polymer abbreviation | Monomer unit (3) |
| --- | --- |
| X-1 | M (1) Et |
| X-2 | M (1) iP |
| X-3 | M (1) sB |
| X-4 | M (2) Et |
| X-5 | M (2) iP |
| X-6 | M (2) sB |

(Preparation of Pattern Forming Material and Composition for Pattern Formation)

A curing agent was not added to each of the polymers X-1 to X-6 to obtain each of pattern forming materials 1 to 6 (Examples 11 to 16). To each of the obtained pattern forming materials 1 to 6, PGMEA was added so that the content of each of the pattern forming materials was 10 wt %, to prepare compositions for pattern formation.

[Evaluation]

The organic films were formed by using the compositions for pattern formation including the pattern forming materials 1 to 6, and a metallization process was performed by the following method to produce composite films. A metallization property of each organic film and etch resistance of each obtained composite film were evaluated.

(Metallization Property)

The organic films were formed on Si substrates by using the pattern forming materials 1 to 6, and the organic films were each metallized by using TMA to evaluate the metallization property.

The Si substrate after UV exposure cleaning treatment for three minutes was used. Each composition for pattern formation was coated on the Si substrate by spin coating. The number of rotations was adjusted to 2000 to 3500 rpm according to the kind of the polymer, and after the coating, a solvent was removed by drying to form the organic film each having a thickness of approximately 300 nm. Further, 200° C. annealing was performed to proceed a crosslinking reaction. The obtained organic film-attached Si substrate was cut into 15 mm square to form a sample for the metallization process.

The metallization was performed by an atomic layer deposition (ALD) apparatus. Concretely, the metallization was performed in an exposure mode where the sample for the metallization process was placed in the ALD chamber, gas-phase TMA was introduced into the chamber at a predetermined pressure, and a valve was kept closed to maintain the pressure for a predetermined time. Initial pressure was set to 900 Pa, the temperature was set to 250° C. for X-1, X-4, and 200° C. for the other polymers, and the atmosphere was held for 600 seconds. Note that the pressure in the chamber gradually increased as the time elapsed because TMA was decomposed to generate methane. TMA was coordinated to an unshared electron pair in the polymer X or a polymer XR in the organic film through the above-stated operation.

After exposure to TMA, vapor ($H_2O$) was substituted for the gas phase in the chamber to increase the pressure to a predetermined pressure, then the valve was kept closed to maintain the pressure for a predetermined time. An initial pressure was set to 300 Pa, and the atmosphere was held for 200 seconds. The temperature was set the same as the temperature at the TMA exposure. The pressure in the chamber gradually decreased because $H_2O$ was consumed or adhered to a chamber inner wall. After the holding time under the $H_2O$ filled state elapsed, each metallized sample for the metallization process was taken out of the chamber. By this operation, TMA was oxidized to form aluminum hydroxide and aluminum oxide.

Here, the ALD apparatus is used for the above-described metallization process, but the above-described operation is aimed on the infiltration of TMA into the polymer and is not aimed to deposition of an atomic layer on the substrate, what is called atomic layer deposition (ALD). Therefore, exposure time to the metallic compound is longer, and the number of cycles is smaller than those of normal ALD.

(Etch Resistance)

Each of the metallized organic film-attached substrates (each of the composite film-attached substrates) was subjected to reactive ion etching (RIE) using $O_2$ gas or CFA gas. Film thicknesses of the composite film of each composite film-attached substrate before and after the RIE were measured by using an atomic force microscope (AFM), and a film thickness difference before and after the RIE was measured as an etching amount to calculate an etch rate [nm/sec]. Table 2 presents the results. In Table 2, "as spun" presents an etch rate measured under the state before metallization, and "metallized" presents an etch rate measured for each metallized organic film.

(1) $O_2$ RIE

The $O_2$ RIE was performed by using CI-300L (manufactured by SAMCO Inc.) under conditions of power: 50 W, bias: 5 W, flow: 5 sccm, and pressure: 3 Pa.

(2) $CF_4$ RIE

The $CF_4$ RIE was performed by using CI-300L under conditions of power: 50 W, bias: 10 W, flow: 5 sccm, and pressure: 3 Pa.

The etch resistance for the $O_2$ RIE dramatically improves as the degree of metallization increases. The composite film formed of a polymeric material having an ester bond (—C(=O)—O—) on a side chain has high etch resistance to the $O_2$ RIE. It is thought that the metallization likely occurred and the etch resistance for the $O_2$ RIE was increased because there were a lot of carbonyl groups in the component. The etch resistance for the $CF_4$ RIE improves as the degree of metallization increases.

(3) IBE

Ion beam etching (IBE) was performed for each of the metallized organic film-attached substrates (each of the composite film-attached substrates). Film thicknesses of the composite film of each composite film-attached substrate before and after the IBE were measured by using the atomic force microscope (AFM), and a film thickness difference before and after the IBE was measured as an etching amount to calculate an etch rate [nm/sec].

(4) RIE Resistance Assuming Memory Holes

Conditions near RIE of memory holes of a three-dimensional memory were assumed, and etching was performed under a mixed gas condition of $C_4F_4$; 80 sccm, Ar, 100 sccm, $O_2$; 54 sccm, $N_2$; 50 sccm. A film thickness difference before and after the etching was measured as an etching amount to calculate an etch rate [nm/sec].

and 0.1 mmol of azobisisobutyronitrile (AIBN) as a initiator were put into a 100 cc round-bottomed flask, and approximately 5 mL of toluene was added as a solvent. After air in the flask was removed by nitrogen, polymerization was carried out at 100° C. for eight hours. After the reaction was completed, the flask was made open to the atmosphere to terminate the polymerization, and thereafter a reaction solution was dropped in a large excess of methanol to purify polymer components by reprecipitation. The obtained solid was filtered off, and this solid was dried in a vacuum for several days to obtain the desired polymer X.

TABLE 3

| Polymer number | Monomer unit (3) | | Crosslinkable monomer unit | |
|---|---|---|---|---|
| | Monomer kind | Input amount [mmol] | Monomer kind | Input amount [mmol] |
| X-11 | M(1)Et | 9.5 | L1-1M | 0.5 |
| X-12 | M(1)iP | 9.5 | L1-1M | 0.5 |
| X-13 | M(1)sB | 9.5 | L1-1M | 0.5 |
| X-14 | M(2)Et | 9.5 | L1-1M | 0.5 |
| X-15 | M(2)iP | 9.5 | L1-1M | 0.5 |
| X-16 | M(2)sB | 9.5 | L1-1M | 0.5 |

TABLE 2

| Example | Polymer kind | $O_2$ RIE rate (nm/sec) | | $CF_4$ RIE rate (nm/sec) | | Mixed Gas RIE rate (nm/sec) | | IBE rate (nm/sec) | |
|---|---|---|---|---|---|---|---|---|---|
| | | as spun | metallized | as spun | metallized | as spun | metallized | as spun | metallized |
| 11 | X-1 | 0.2 | 0.03 | 0.6 | 0.4 | 0.8 | 0.02 | 0.6 | 0.4 |
| 12 | X-2 | 0.2 | 0.02 | 0.6 | 0.2 | 0.8 | 0.02 | 0.6 | 0.3 |
| 13 | X-3 | 0.3 | 0.02 | 0.6 | 0.2 | 0.8 | 0.01 | 0.6 | 0.3 |
| 14 | X-4 | 0.3 | 0.02 | 0.6 | 0.5 | 0.7 | 0.04 | 0.7 | 0.4 |
| 15 | X-5 | 0.3 | 0.02 | 0.7 | 0.5 | 0.7 | 0.04 | 0.7 | 0.4 |
| 16 | X-6 | 0.3 | 0.02 | 0.7 | 0.3 | 0.7 | 0.04 | 0.7 | 0.3 |

Examples 21 to 26

A crosslinkable polymer X constituted of only the monomer unit (3) and the crosslinkable monomer unit was produced. A composition for pattern formation was prepared by using a pattern forming material containing the obtained polymer X and an organic solvent to be evaluated.

(Polymerization of Crosslinkable Polymer X)

Each constituent monomer of the monomer unit (3) and each constituent monomer of the crosslinkable monomer unit presented in Table 3 were polymerized according to the following procedure to obtain crosslinkable polymers X-1 to X-16 by using amounts presented in Table 3. A yield of each of the obtained polymers X-1 to X-16 was approximately 80 to 90%. The crosslinkable monomer unit where R was a methyl group in the monomer unit L1-1 (denoted as "L1-1M" in Table 3.) was used as the crosslinkable monomer unit.

The constituent monomer of the monomer unit (3), the constituent monomer of the crosslinkable monomer unit, (Preparation of Pattern Forming Material and Composition for Pattern Formation)

As presented in Table 4, citric acid (denoted as "CA" in Table 4) as a curing agent was added to each of the polymers X-11 to X-16 at a ratio of 0.5 mol with respect to 1 mol of a glycidyl group in each of the polymers X, to form each of pattern forming materials 11 to 16 (Examples 21 to 26). Regarding each of the obtained pattern forming materials 11 to 16, PGMEA was added so that the content of each of the pattern forming materials was 10 wt %, to prepare each composition for pattern formation.

[Evaluation]

The organic films were formed by using the compositions for pattern formation including the pattern forming materials 11 to 16, and a metallization process was performed by a similar method as Examples 11 to 16 to produce composite films. The metallization property of each organic film and the etch resistance of each obtained composite film were evaluated. Table 4 presents the results.

TABLE 4

| Example | Pattern forming material Polymer kind | Pattern forming material Curing agent | O$_2$ RIE rate (nm/sec) as spun | O$_2$ RIE rate (nm/sec) metallized | CF$_4$ RIE rate (nm/sec) as spun | CF$_4$ RIE rate (nm/sec) metallized | Mixed Gas RIE rate (nm/sec) as spun | Mixed Gas RIE rate (nm/sec) metallized | IBE rate (nm/sec) as spun | IBE rate (nm/sec) metallized |
|---|---|---|---|---|---|---|---|---|---|---|
| 21 | X-11 | CA | 0.2 | 0.03 | 0.6 | 0.4 | 0.8 | 0.02 | 0.6 | 0.4 |
| 22 | X-12 | CA | 0.3 | 0.03 | 0.6 | 0.2 | 0.8 | 0.02 | 0.6 | 0.3 |
| 23 | X-13 | CA | 0.4 | 0.02 | 0.7 | 0.2 | 0.8 | 0.01 | 0.6 | 0.3 |
| 24 | X-14 | CA | 0.3 | 0.02 | 0.6 | 0.6 | 0.7 | 0.05 | 0.8 | 0.4 |
| 25 | X-15 | CA | 0.3 | 0.02 | 0.7 | 0.5 | 0.8 | 0.04 | 0.7 | 0.5 |
| 26 | X-16 | CA | 0.3 | 0.02 | 0.7 | 0.3 | 0.7 | 0.04 | 0.7 | 0.3 |

As presented in Table 2 and Table 4, it is clear that the composite film formed by using this pattern forming material has high etch resistance. In particular, it was verified that all of the composite films exhibited higher etch resistance after metallization compared to conventional ones under the etching conditions using the mixed gas near the RIE process to form the memory holes of the three-dimensional memory.

A method for forming a pattern in the embodiment is added to the following.

1. A method for forming a pattern, comprising:
    forming an organic film on a film to be processed by using a pattern forming material;
    patterning the organic film, and;
    forming a composite film by infiltrating a metallic compound into the patterned organic film to obtain a mask pattern formed of the composite film, wherein
    the pattern forming material contains a polymer including a monomer unit represented by a general formula (3) described below,

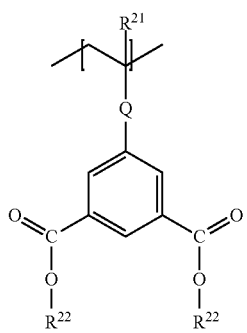

(3)

wherein, $R^{21}$ is a hydrogen atom or a methyl group, each $R^{22}$ independently is a hydrocarbon group having 2 to 14 carbon atoms where a carbon is primary carbon, secondary carbon or tertiary carbon, and Q is a single bond or a hydrocarbon group having 1 to 20 carbon atoms which may include an oxygen atom, a nitrogen atom, or a sulfur atom between carbon-carbon atoms or at a bond terminal, and a halogen atom may be substituted for the hydrogen atom.

2. The method according to clause 1, wherein each $R^{22}$ independently is an ethyl group, an n-propyl group, an isopropyl group, an n-butyl group, an isobutyl group, an s-butyl group, or a t-butyl group.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A polymer including at least one of:
    a monomer unit selected from a monomer unit derived from a compound represented by a general formula (1) described below,

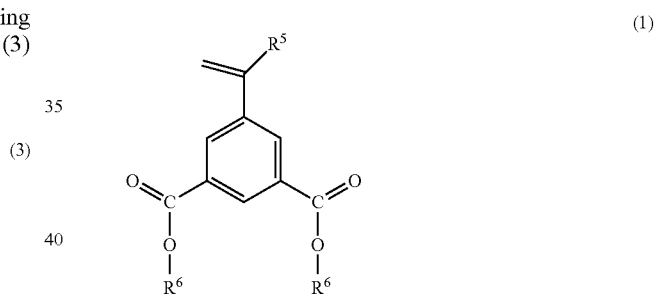

(1)

wherein, $R^5$ is a hydrogen atom or a methyl group, each $R^6$ independently is an ethyl group, an n-propyl group, an isopropyl group, an n-butyl group, an isobutyl group, or an s-butyl group, and a monomer unit derived from a compound represented by a general formula (2) described below,

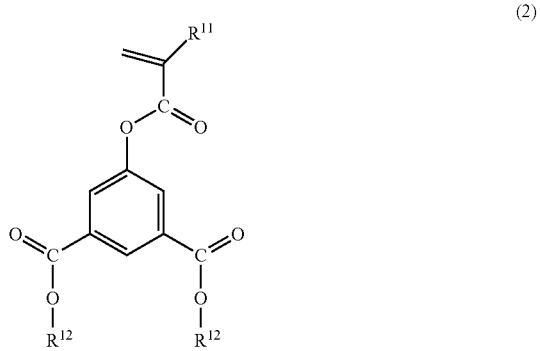

(2)

wherein, $R^{11}$ is a hydrogen atom or a methyl group, each $R^{12}$ independently is a methyl group, an ethyl group, an n-propyl group, an isopropyl group, an n-butyl group, an isobutyl group, an s-butyl group, or a t-butyl group.

* * * * *